United States Patent [19]

Kollonitsch et al.

[11] 4,028,405

[45] June 7, 1977

[54] FLUORINATED AMINO ACIDS

[75] Inventors: Janos Kollonitsch, Westfield; Frederick M. Kahan, Rahway, both of N.J.

[73] Assignee: Merck & Co., Inc., Rahway, N.J.

[22] Filed: June 7, 1976

[21] Appl. No.: 693,819

Related U.S. Application Data

[63] Continuation of Ser. No. 514,865, Oct. 15, 1974, abandoned, which is a continuation of Ser. No. 238,684, March 27, 1972, abandoned, which is a continuation of Ser. No. 149,814, June 3, 1971, abandoned.

[52] U.S. Cl. .......................................... 260/534 C
[51] Int. Cl.$^2$ ...................................... C07C 101/10
[58] Field of Search .............................. 260/534 C

[56] References Cited

UNITED STATES PATENTS

| | | | |
|---|---|---|---|
| 3,839,170 | 10/1974 | Kollonitsch | 260/534 C |
| 3,956,367 | 5/1976 | Kollonitsch | 260/534 C |

FOREIGN PATENTS OR APPLICATIONS

| | | | |
|---|---|---|---|
| 818,335 | 7/1974 | Belgium | 260/534 C |
| 831,760 | 1/1976 | Belgium | 260/534 C |
| 835,358 | 5/1976 | Belgium | 260/534 C |
| 39-30152 | 1964 | Japan | 260/534 C |

OTHER PUBLICATIONS

Rittenberg et al., "J. Biol. Chem.," vol. 125 (1938), pp. 1–12.
Yson et al., "Chem. Abstracts," vol. 54 (1960), Cols. 12096–12098.
Lettre et al., "Chem. Abstracts," vol. 68 (1968), 22229n.
Komkors et al., "Chem. Abstracts," vol. 37 (1943), 4412.
Winnick et al., "Chem. Abstracts", vol. 58 (1960), Col. 8160.
Abstracts 100, 101, 102, 103, 15th Interscience Conf. on Antimicrobial Agents and Chemotherapy held in Washington D. C., Sept. 1975.

*Primary Examiner*—Joseph E. Evans
*Attorney, Agent, or Firm*—Hesna J. Pfeiffer; Julian S. Levitt

[57] ABSTRACT

Deutero analogs of 3-fluoro-D-alanine prepared by direct photofluorination of the D-amino acids demonstrate in vivo and in vitro antibacterial activity against both gram negative and gram positive microorganisms. Deuters analogs of 3-fluoro-L-alanine and 3-fluoro-D,L-alanine also demonstrate useful in vitro activity.

3 Claims, No Drawings

FLUORINATED AMINO ACIDS

RELATIONSHIP TO PRIOR APPLICATIONS

This application is a continuation application of copending application, U.S. SN 514,865, filed Oct. 15, 1974, now abandoned, which is a continuation of copending application, U.S. SN 238,684, filed Mar. 27, 1972, now abandoned, which is a continuation of copending application, U.S. SN 149,814, filed June 3, 1971, now abandoned.

It is concerned with fluorinated amino acids and in particular with α'-fluoro-amino acids and pharmaceutically acceptable salts. Even more particularly it is concerned with the group of compounds having the following structural formula:

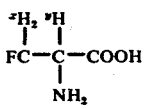

wherein X is 1 or 2 and Y is 2 and represents the atomic weight so that the substituents carrying these designations are either hydrogen or deuterium. The symbols D and L refer to the optical isomers. Included in this group of compounds are for example, 2-$^2$H-3-fluoro-D-alanine and 2,3,3$^2$H-3-fluoro-D-alanine, and their pharmaceutically acceptable salts.

The in vitro antibacterial activity of the optical isomers is comparable. Yet in vivo the isomers differ markedly. The D-isomer retains its antibacterial properties and serves to protect the infected animal whereas the L-isomer appears to be lacking in ability to protect bacterially infected animals and indeed is lethal to those animals at only moderate dose levels.

The novel compounds of this invention and their salts are antibacterial agents, which are useful in inhibiting the growth of pathogenic bacteria of both gram-positive and gram-negative genera such as *Streptococcus*, *Escherichia*, *Staphylococcus*, *Salmonella*, *Pseudomonas*, *Diplococcus*, *Klebsiella*, *Proteus*, *Mycobacterium*, *Vibrio*, *Pasteurella* and *Serratia*, as well as antibiotic resistant strains thereof. Illustrative of such pathogens are *Escherichia coli*, *Salmonella schottmuelleri*, *Proteus vulgaris*, *Proteus mirabilis*, *Pseudomonas aeruginosa*, *Staphylococcus aureus* and *Streptococcus pyogenes*. Thus the novel compounds of this invention and their salts can be used as antiseptic agents to remove susceptible organisms from pharmaceutical, dental and medical equipment and can also be used in other areas subject to infection by such organism.

The D-isomers of the novel compounds and salts are particularly valuable because not only do they have the above mentioned utility but they are also useful in the treatment of diseases caused by the above organisms in man and animals and can be administered in a wide variety of therapeutic dosages in conventional vehicles as, for example, by oral administration in the form of a capsule or tablet or in a liquid solution or suspension. Suitable formulations may include diluents, granulating agents, preservatives, binders, flavoring agents and coating agents which are well known to those skilled in this particular art and the dosage of the products may be varied over a wide range. For example, doses would range from about 250 mg. to about 500 mg. two to four times daily of active ingredient per 70 kgm. adult human. A growing feedlot animal on growth permittant therapy should receive about 100 g./ton of complete food. Alternatively, they may be administered parenterally by injection in a sterile excipient.

It has further been found that deuteration provides novel deutero analogs that are significantly less susceptible to attack by D-amino acid oxidase yet retain the antibacterial potency of the parent compound. The in vivo activity is thereby increased and sustained.

The novel fluorinated amino acids of this invention are prepared by a process which comprises treating the substrate with a fluoroxyperfluoroalkane or fluoroxypentafluorosulfur under the influence of a free radical initiator such as light which includes ultraviolet light, ionizing radiations such as α-rays or microwaves, or chemical chain initiators such as azo compounds, for example, azo-bis-isobutyronitrile or combinations of such free radical initiators. The preferred mode of operation is to dissolve the substrate in a suitable solvent which is inert to the fluorination reaction such as liquid hydrogen fluoride, fluorosulfonic acid, trifluoroacetic acid or sulfuric acid; expose the solution to the free radical initiator; with vigorous stirring and maintenance of temperature, admit the required amount of the fluoroxy reagent slowly to the reaction mixture; and continue agitation and irradiation until reaction is complete.

Because of the low boiling point of the reagents it is convenient to conduct the reaction at temperatures as low as −80° C. in which case the reaction proceeds at atmospheric pressure.

A suitable reaction vessel for atmospheric pressure reactions is one machined from a Kel-F rod equipped with an ultraviolet-transparent window. Alternatively the reaction can be conducted in a pressure vessel such as a Hastelloy bomb or a steel bomb with a platinum lining, in which case higher temperatures, for instance up to about 100° C. can be employed. In such case the use of α-rays or x-rays as free radical initiator is convenient, as these high energy rays penetrate the wall of the reactor.

The above described process can be performed by conventional batch techniques, or alternatively it can be run in a continuous manner in a tubular reactor either with or without packing such as Raschig rings, saddles or the like through which the substrate or its solution and the fluorinating agent are pumped, preferably in a countercurrent fashion while being exposed to radical generating radiation.

A convenient source of radiation for radical generation was found to be a Hanovia mercury-xenon arc lamp No. 9778–1, run by a 1000 W. power supply. The lamp was mounted in a Schoeffel LH 15 1-N Projector equipped with a quartz condenser lens and a heat filter (water).

EXAMPLE 1

3-Fluoro-D-alanine

Into a solution of 1.822 g. of D(−) alanine in 45 ml. of liquid HF, 0.6 g. of fluoroxytrifluoromethane gas was passed over a period of about 1 hour while being magnetically stirred, cooled in a dry-ice-acetone bath and irradiated by ultraviolet light. After 80 minutes further ultraviolet irradiation, 2 g. more of fluoroxytrifluoromethane gas was passed in while being ultraviolet irradiated over one and a half hours, followed by another 1 hour ultraviolet irradiation.

The solvent was removed by blowing through it a stream of nitrogen gas. The residue was dissolved in ice-water and a sample of it was analyzed in the Spinco-Beckman amino acid analyzer, indicating a 41% yield of 3-fluoro-D-alanine, and 32% of unreacted starting material. For isolation, the mixture was chromatographed on Dowex 50 × 8 cation exchange resin ($H^+$ form) (a polystyrene nuclear sulfonic acid resin sold by Dow Chemical Co., Midland, Michigan). For elution, 2N HCl was employed. From the appropriate fractions, by evaporation in vacuo, pure 3-fluoro-D-alanine hydrochloride was obtained. 3-fluoro-D-alanine was liberated from the hydrochloride in water-pyridine-isopropanol mixture, m.p. 166°–168° C. (dec.); $[\alpha]_D^{20}$, −9.3° (C,2 in 1N-HCl).

EXAMPLE 2

3-Fluoro-L-alanine

Employing the procedure of Example 1, but substituting for the D-alanine used therein, an equal amount of L-alanine, there is produced 3-fluoro-L-alanine, m.p. 167°–168° C., $[\alpha]_D^{20}$ + 9.1 (C, 2, in 1N HCl).

EXAMPLE 3

2-$^2$H-3-Fluoro-D-alanine

Deuterium was incorporated into the alpha position of D-alanine by exposing L-alanine to the action of alanine racemase in $^2H_2O$, employing for that purpose a crude enzyme preparation from *Staphylococcus aureus* [E. Ito and J. L. Strominger, *J. Biol. Chem.*, 237, 2689 (1962)] that had been exhaustively dialysed against buffered $^2H_2O$. After recovery of salt-free alanine from the reaction mixture by ion-exchange procedures, the D-alanine which was formed was separated from input L-alanine by the sequence of chemical N-acetylation and specific enzymic deacetylation of the L-isomer with hog renal Acylase I as described by J. P. Greenstein and M. Winitz in *Chemistry of the Amino Acids*, Vol. 3, p. 1831 (Wiley and Sons, New York, 1961). The 2-$^2$H-D-alanine obtained following acid hydrolysis of the acetylated residue was 95% enriched for $^2$H specifically in the 2 position (as determined by NMR) and contained less than 1% L-alanine as enzymatically determined with L-alanine: oxoglutarate transaminase.

Employing the procedure of Example 1, but substituting for the D-alanine used therein, an equivalent amount of the 2-$^2$H-D-alanine, produced as above, there was obtained 2-$^2$H-3-fluoro-D-alanine, m.p. 169° C., $[\alpha]_D^{20}$− 9.2 (C, 2, in 1N HCl).

EXAMPLE 4

3,3,2-$^2$H-3-Fluoro-D-alanine 3,3,3-$^2$H-D-Alanine was resolved from the commercially available perdeutero alanine racemate by the sequence of chemical N-acetylation and enzymic deacetylation of the L-moiety as described in Example 3.

Photofluorination of the perdeutero-D-alanine by the procedure described in Example 1, gives 3,3,2-$^2$H-3-fluoro-D-alanine.

What is claimed is:

1. A compound of structural formula

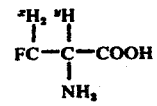

D− or L− or D,L−
wherein X is 1 or 2 and y is 2.

2. 2-Deutero-3-fluoro-D-alanine.
3. 2,3,3-Trideutero-3-fluoro-D-alanine.

* * * * *

UNITED STATES PATENT AND TRADEMARK OFFICE
CERTIFICATE OF CORRECTION

PATENT NO. : 4,028,405

DATED : June 7, 1977

INVENTOR(S) : JANOS KOLLONITSCH et al.

It is certified that error appears in the above-identified patent and that said Letters Patent are hereby corrected as shown below:

On cover page of patent the author of the 2nd reference under "OTHER PUBLICATIONS" should be -- Yuan et al. -- instead of "Yson et al."

On cover page of patent the author of the 4th reference under "OTHER PUBLICATIONS" should be -- Konikova et al. -- instead of "Komkors et al."

On the cover page of patent under the "ABSTRACT" at the 5th line should be -- Deutero -- instead of "Deuters".

At Col. 1, line 20, below the present formula and above the definition of "X", insert -- D or L or D,L --.

Signed and Sealed this

Sixth Day of September 1977

[SEAL]

Attest:

RUTH C. MASON
Attesting Officer

LUTRELLE F. PARKER
Acting Commissioner of Patents and Trademarks